(12) United States Patent
Fidel et al.

(10) Patent No.: US 7,090,643 B2
(45) Date of Patent: Aug. 15, 2006

(54) ULTRASONIC IMAGING DEVICE, SYSTEM AND METHOD OF USE

(75) Inventors: Howard F. Fidel, Irvington, NY (US); Raul F. Gutierrez, Fort Lee, NJ (US)

(73) Assignee: 3G Ultrasound, Inc., Ramsey, NJ (US)

( * ) Notice: Subject to any disclaimer, the term of this patent is extended or adjusted under 35 U.S.C. 154(b) by 0 days.

(21) Appl. No.: 10/763,341

(22) Filed: Jan. 23, 2004

(65) Prior Publication Data
US 2004/0152986 A1    Aug. 5, 2004

Related U.S. Application Data

(60) Provisional application No. 60/442,034, filed on Jan. 23, 2003.

(51) Int. Cl.
*A61B 8/12* (2006.01)

(52) U.S. Cl. ...................................... 600/447; 600/463

(58) Field of Classification Search ................ 600/440, 600/441, 443, 447, 462–467; 128/916
See application file for complete search history.

(56) References Cited

U.S. PATENT DOCUMENTS

| | | | | |
|---|---|---|---|---|
| 5,103,129 A | * | 4/1992 | Slayton et al. ............... 310/335 |
| 5,121,361 A | | 6/1992 | Harrison, Jr. et al. | |
| 5,398,691 A | * | 3/1995 | Martin et al. ................ 600/463 |
| 5,471,988 A | * | 12/1995 | Fujio et al. .................. 600/439 |
| 5,842,991 A | * | 12/1998 | Barabash ...................... 600/443 |
| 5,860,926 A | * | 1/1999 | Barabash et al. ............ 600/443 |
| 5,876,345 A | * | 3/1999 | Eaton et al. .................. 600/466 |
| 5,905,692 A | | 5/1999 | Dolazza et al. | |
| 6,045,508 A | * | 4/2000 | Hossack et al. ............. 600/447 |
| 6,059,731 A | * | 5/2000 | Seward et al. ............... 600/459 |
| 6,120,453 A | * | 9/2000 | Sharp ........................... 600/463 |
| 6,171,248 B1 | | 1/2001 | Hossack et al. | |
| 6,422,997 B1 | | 7/2002 | Green et al. | |
| 6,423,002 B1 | * | 7/2002 | Hossack ....................... 600/439 |
| 6,428,479 B1 | | 8/2002 | Aksnes et al. | |
| 6,432,035 B1 | | 8/2002 | Ravins et al. | |
| 6,454,696 B1 | | 9/2002 | Kindlein et al. | |
| 6,511,427 B1 | * | 1/2003 | Sliwa et al. ................. 600/438 |
| 6,685,644 B1 | * | 2/2004 | Seo et al. ..................... 600/447 |
| 6,709,397 B1 | | 3/2004 | Taylor | |

OTHER PUBLICATIONS

Transrectal Probes, EUP-U33, EUP-U322, EUP-CC331, Hitachi Corp., dates unknown.
Linear Scan 3D Bi-Plane Transrectal Ultrasound Probe, Envisioneering Product Development Corporation, Oct. 19, 2000 (8 Pages) (see U.S. Patent No. 6,709,397 cited above).

* cited by examiner

*Primary Examiner*—Francis J. Jaworski
(74) *Attorney, Agent, or Firm*—David Aker

(57) ABSTRACT

An ultrasonic probe comprises an elongate structure having a longitudinal axis; a first array of ultrasonic transducer elements extending along an outer surface of the elongate structure in a direction generally parallel to the longitudinal axis; a second array of ultrasonic transducer elements extending along the outer surface of the elongate structure in a direction generally parallel to the longitudinal axis; and a third array of ultrasonic transducer elements extending about the elongate structure in a direction so that it images a plane perpendicular to that imaged by at least one of the first array and the second array, the third array being disposed in a space between the first array and the second array. An electronics module for use with the probe, and an additional probe, to produce internal images of a patient.

27 Claims, 4 Drawing Sheets

ULTRASONIC IMAGING DEVICE, SYSTEM AND METHOD OF USE

This application claims priority under 35 U.S.C. §119(e) from U.S. provisional patent application Ser. No. 60/442,034, filed on Jan. 23, 2003, which is incorporated herein by reference, in its entirety.

BACKGROUND OF THE INVENTION

1. Field of the Invention

The present invention relates to apparatus used for ultrasonic imaging. More particularly, it relates to apparatus for simultaneous imaging in both longitudinal and transverse views. More specifically, it relates to apparatus for imaging for purposes of medical diagnosis and treatment, especially for diagnosis and treatment of organs such as the prostate.

2. Prior Art

There are various situations in which it is necessary to do ultrasonic imaging to assist in medical diagnosis and treatment. For example, prostate cancer is one of the most common cancers found in men. Treatment options include "watchful waiting", hormonal therapy, brachytherapy, or surgery. Three types of surgery are used. The classical "open" procedure, radical prostetectomy, and the newly developed laproscopic and cryosurgery procedures. All procedures have risks. Both the open procedures and the laproscopic procedures have significant risks of causing impotence and incontinence. With both brachytherapy, and cryosurgery the prostate is left in vivo, and therefore the risk of complications is much lower, and the recovery time is quicker.

In brachytherapy, trains of seeds are implanted in rows in the prostate. Cryosurgery is done in a similar fashion, except that cooling needles are inserted in eight to twelve locations in the prostate. Cold gases are circulated through the needles, and the prostate is monitored by ultrasound imaging for the formation of ice balls, which indicates proper operation of the device. Both of these procedures may be preformed under local anesthetic.

As illustrated in FIG. 1, ultrasound guidance is used in order to properly locate the needle holding the seeds for brachytherapy or the needles for cryosurgery. In FIG. 1, those skilled in the art will recognize the following bladder B, prostate P, urethra U, rectum R, perianal wall Pe, operator 10, ultrasonic probe 12, needle grid block 14, needle 16, needle core 18, and seeds 20.

As illustrated in FIG. 2, in the prior art, the typical bi-plane ultrasonic probe 22 used has a linear transducer array 24 to image the sagital or longitudinal view, and a micro-convex curved array 26 for the transverse view. The linear array is usually 50 mm long, and is not long enough to visualize the entire prostate in many patients.

As illustrated in FIG. 3, the micro-convex array 26 is at the end of the probe, and its imaging plane 28 does not intersect the linear array's imaging plane 30. This causes the operator to have to constantly move the probe to different positions along the rectum during the procedure. This is time consuming, and more importantly, causes the prostate to move, leading to more uncertainty as to where the seeds are being placed.

SUMMARY OF THE INVENTION

It is an object of the invention to provide an ultrasonic probe that allows the entire prostate to be visualized at once.

It is a further object of the invention to provide an ultrasonic probe that may be used to place the transverse scan in the middle of the prostate, thus eliminating the need to change the longitudinal position of the transducer along the rectum, and requiring rotation, which does not move the prostate significantly.

It is yet another object of the invention to allow for more accurate and quicker needle placement for brachytherapy and cryosurgery when using a standard brachytherapy and cryosurgery apparatus.

It is still another object of the invention to provide an ultrasonic probe that allows for the entire prostate to be imaged simultaneously in both longitudinal and transverse views.

These objects and others are achieved in accordance with the invention by providing a bi-plane transducer where three independent arrays are mounted. There are two curved arrays typically subtending 30 degrees of arc of typically 60 mm radius mounted longitudinally on the housing, with a micro-convex array of typically 10 mm radius mounted transversely between the two larger curved arrays.

The ultrasound system used with this ultrasonic probe can be used to scan all three arrays sequentially. The two convex arrays are used to create one continuous image of the longitudinal plane. The micro-convex transducer images the transverse plane. Both images can be displayed simultaneously on the system monitor. At least one high voltage multiplexer integrated circuit may be built into the handle to switch the system electronics between the three different arrays of the probe. At least one additional multiplexer may be used to switch between the above mentioned probe and another probe.

The present invention is also directed to the combination of the new ultrasonic probe described herein, and an electronics package or module to which the probe is connected. As is known in the art, such package or module serves to excite and control the transducer arrays of the ultrasonic probe, process signals representative of ultrasonic reflections received by the transducer arrays from structures within a subject or patient, form images in accordance with the processed signals, and display the images for viewing by appropriate personnel.

The invention is also directed to a method of using an ultrasonic probe, and in particular, the ultrasonic probe in accordance with the invention, and the associated electronics package or module (in combination, the ultrasonic system) to image two intersecting planes within the subject or patient. Preferably, an entire organ (such as the prostate) is viewed, without having to reposition the probe (along the length of the rectum, in the case of the prostate).

Thus, the invention is directed to an ultrasonic probe comprising an elongate structure having a longitudinal axis; a first array of ultrasonic transducer elements extending along an outer surface of the elongate structure in a direction generally parallel to the longitudinal axis; a second array of ultrasonic transducer elements extending along the outer surface of the elongate structure in a direction generally parallel to the longitudinal axis; and a third array of ultrasonic transducer elements extending about the elongate structure in a direction so that it images a plane perpendicular to that imaged by at least one of the first array and the second array, the third array being disposed in a space between the first array and the second array.

The first array, the second array and the third array are preferable outwardly convex. The third array preferably has a radius of curvature smaller than that of the first array and the second array. The first array and the second array may be configured so that beams formed by the first array and the second array subtend substantially thirty degrees of arc. The third array may be configured so that a beam formed by the third array subtends substantially one hundred eighty degrees of arc.

The probe may further comprise a multiplexer for multiplexing connections to each of the first array, the second array and the third array. The multiplexer may be disposed within the elongate structure.

The first array and the second array are preferably aligned so as to image a portion of a substantially continuous plane perpendicular to the plane imaged by the third array.

The invention is also directed to the above described probe in combination with a second probe, the second probe being capable of positioning so as to imaging in a plane perpendicular to a plan imaged by the first array and a plane imaged by the second array.

The invention is also directed to one or both of the above described probes in combination with an electronics module, comprising excitation circuitry for providing excitation energy to the probe; receiving circuitry for processing signals received by the probe; signal processing circuitry for processing signals from the receiving circuitry to produced processed image signals; and a display for displaying the processed image signals. The combination may further comprise at least one of: frequency setting circuitry for setting a frequency of the excitation energy; depth control circuitry for controlling the depth of images produced on the display; gain control circuitry for controlling gain of the receiving circuitry; and steering and focus control circuitry as a component of the signal processing circuitry for controlling the manner of operation of the signal processing circuitry. The excitation circuitry may comprise a table memory for providing values of waveforms used to excite transducer elements of the probe. The combination may further comprising analog to digital converters as components of the signal processing circuitry for converting analog signals from the receiving circuitry into digital signals.

The invention is also directed to an ultrasonic imaging system comprising: a first probe having an elongate structure having a longitudinal axis; at least a first array of ultrasonic transducer elements extending along an outer surface of the elongate structure in a direction generally parallel to the longitudinal axis; an additional array of ultrasonic transducer elements extending about the elongate structure in a direction so that it images a plane perpendicular to that imaged by the at least one first array; a second probe having a further transducer array, the second probe capable of being positioned so as to imaging in a plane perpendicular to a plan imaged by the first array and the plane imaged by the additional array; and an electronics module, the module having the components mentioned above, including the excitation circuitry, receiving circuitry, signal processing circuitry; and a display for displaying processed image signals.

The first probe may further comprise a second array of ultrasonic transducer elements extending along the outer surface of the elongate structure in a direction generally parallel to the longitudinal axis, the second array also being excited by the excitation circuitry.

The additional array is preferably disposed between the first array and the second array.

The system may further comprise at least one multiplexer for connecting each of the first array, the additional array and the further array to the electronics module for display of images.

The at least one multiplexer may comprise a first multiplexer for switching the electronics module between the first probe and the second probe; and a second multiplexer for switching between transducer arrays of the first probe.

The first multiplexer may be a four to one multiplexer, which switches to a first half of transducer element of the further array, a second half of transducer elements of the further array, a first half of transducer element of a selected one of the arrays in the first probe, and a second half of transducer elements of the selected array in the first probe. The second multiplexer may switch the selected array to be one of the first array and the additional array. When the probe comprises a second array extending along the outer surface of the elongate structure, the second array may also be excited by the excitation circuitry, and the second array may be one of the selected arrays.

The invention is also directed to a method for medical ultrasonic imaging comprising placing a first probe having transducer arrays which image in two mutually perpendicular directions in a body cavity of a patient; placing a second probe on an exterior surface of the patient so that a transducer array of the second probe produces an image in a plane perpendicular to each of the two mutually perpendicular planes; exciting the probes; and forming images using signals from the probe to visualize structures within the patient. The first probe may have the structure described above.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
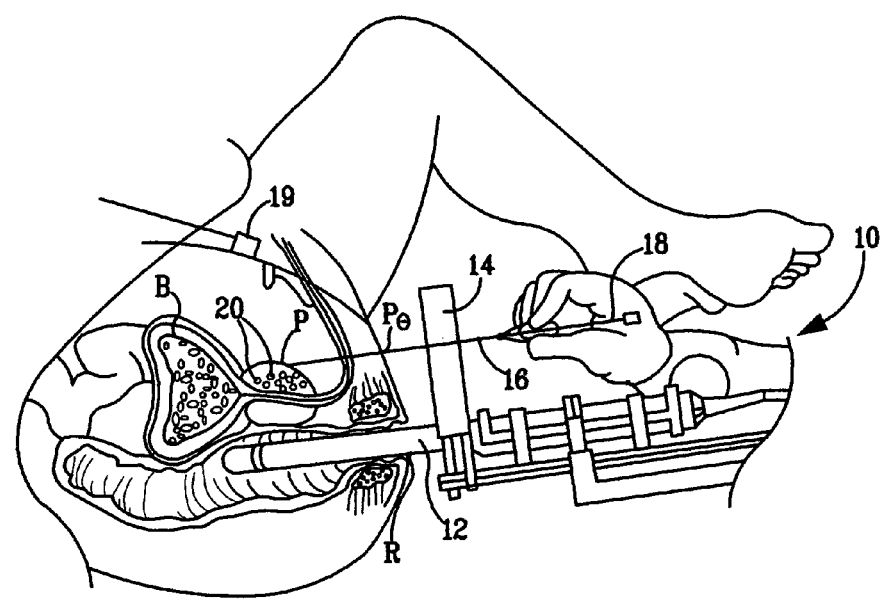
FIG. 1 is a cross-sectional view of a patient with an ultrasonic probe in the rectum held in a brachytherapy device, and with an additional imaging probe.
Figure 2:
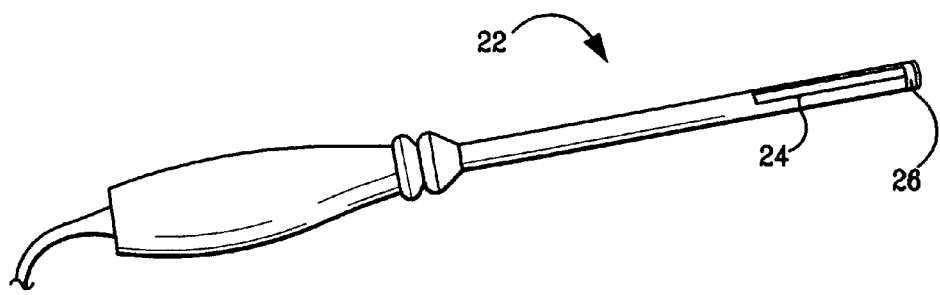
FIG. 2 is a perspective view of a prior art ultrasonic probe with a prior art transducer assembly.
Figure 3:
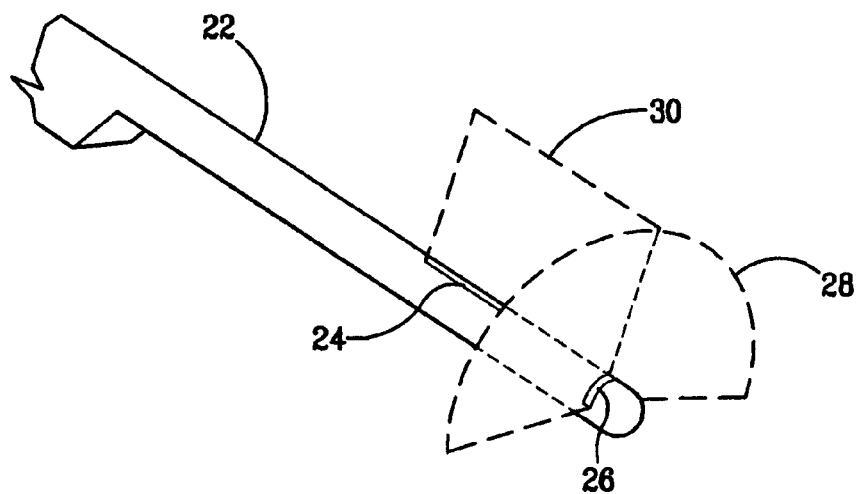
FIG. 3 illustrates the scan planes of the prior art device of FIG. 1.

Referring again briefly to FIG. 1, in accordance with the invention, an additional ultrasonic imaging probe 19 may be placed on the abdominal wall of the patient 21 to image the prostate P from above. Probe 19 may have an array of, for example 128 transducers, in a flat or slightly concave configuration, and thus may be suited to image structures through the abdominal wall of the patient. The coordination of images produced by ultrasonic probe 42 and probe 19 is explained below with respect to FIG. 7. Due to the location of probe 19, with the consequent need for the ultrasound produced and received by probe 19 to traverse a larger distance to and from the prostate than the ultrasound from probe 42, probe 19 may operate at a frequency lower than that used to excite the elements of the transducers of probe 42, or, in some applications, at the same frequency.

Figure 4:
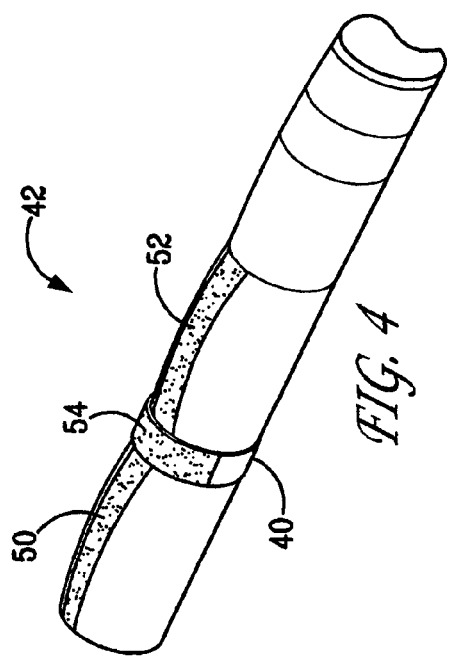
FIG. 4 is a perspective view of the operative end of an ultrasonic probe in accordance with the invention.

Referring to FIG. 4, there is shown a perspective view of the operative or distal end portion 40 of an ultrasonic probe 42 incorporating features of the present invention. Although the present invention will be described with reference to the single embodiment shown in the drawings, it should be understood that the present invention can be embodied in many alternate forms of embodiments. In addition, any suitable size, shape or type of elements or materials could be used.

Figure 5:
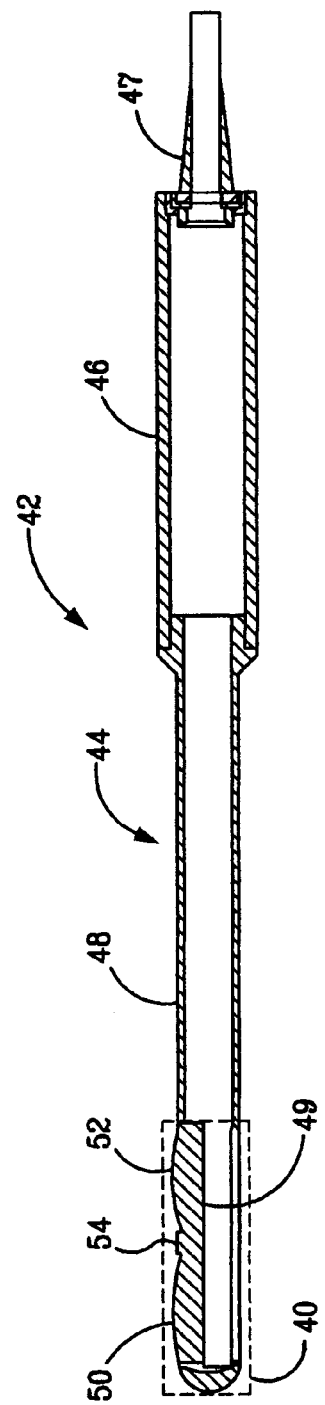
FIG. 5 is a cross sectional view of the embodiment of the invention illustrated in FIG. 4.

Referring also to FIG. 5, ultrasonic probe 42 includes a substantially hollow probe housing 44 having a handle 46, a flexible cable guide 47 for a multi-wire cable (not shown in FIG. 5) a connecting tube 48, and end portion 40. These components (except for cable guide 47) may be constructed of a high strength engineering plastic, which retains its properties after multiple exposures to the heat required for cleaning and sterilization. End portion 40 has a solid insert 49, formed of an insulating material, and designed to support appropriate connecting wires (not shown) and three transducer arrays, as described below.

The three transducer arrays of end portion 40 are for emitting and receiving ultrasound for the purpose of imaging the organs of a patient, and in particular, the prostate of a patient. These transducer arrays include a first convex array 50, a second convex array 52, and a micro-convex array 54.

Transducer arrays 50 and 52 may each comprise 96 piezoelectric elements, having a pitch of 0.327 mm, an elevation of 5 mm, and a focal distance of 30 mm. Each array may subtend 30 degrees of arc, of a 60 mm radius of curvature. The frequency of resonance of the piezoelectric elements may be 6.5 MHz.

Micro-convex transducer array 54 may include 128 elements. Alternatively, it may include 96 elements on a pitch of 0.215 mm, having an elevation of 5 mm and a focal distance of 30 mm, with the beam formed subtending an angle of 180 degrees. The frequency of resonance of the piezoelectric elements may be 6.5 MHz.

As noted above, multiplexing electronics may be located in handle 46 of housing 44. A cable (not shown in FIG. 5) having a 156 pin connector, such as a Cannon ZIF connector, may be used to connect the electronics to an electronics module (FIG. 7) so that images may be generated and viewed.

Figure 6:
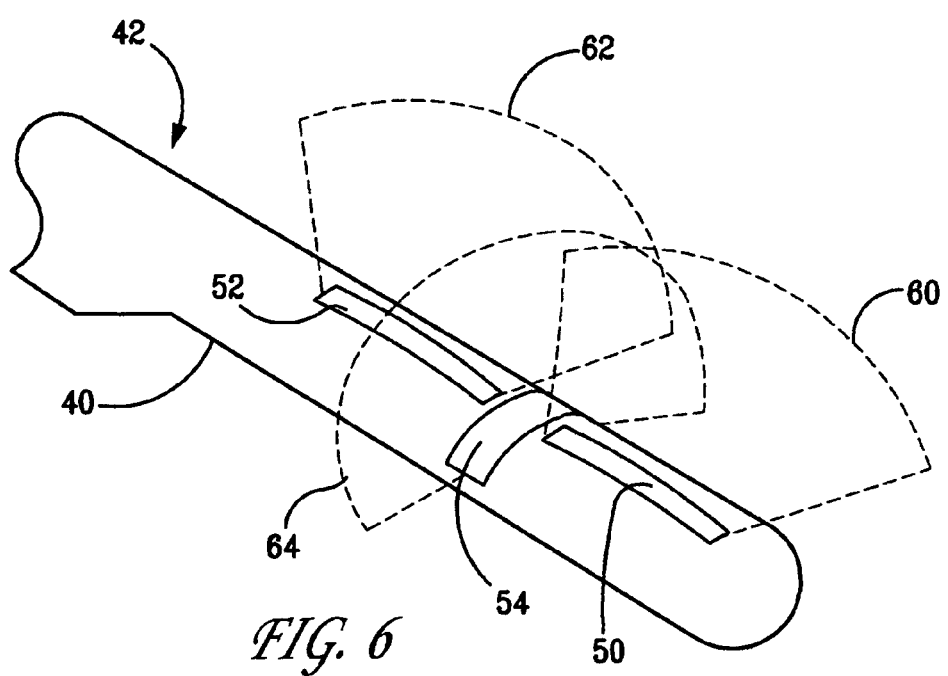
FIG. 6 illustrates the scan planes of the ultrasonic probe in accordance with the invention.

FIG. 6 illustrates the relationship between the sagital or longitudinal scan planes 60 and 62 generated by arrays 50 and 52 respectively, and the transverse scan 64 generated by micro-convex curved array 54. It is noted that scan planes 60 and 62 are co-planar and partially overlap, thus permitting the entire prostate to be imaged along a single longitudinal plane without moving probe 42 in the rectum of the patient. Micro-convex transducer array 54 provides an image in a transverse scan plane 64 that is perpendicular to scan planes 60 and 62. The location of transducer array 54 between transducer arrays 50 and 52 means that the center of the prostate may be imaged in the transverse plane at the same time as the entire prostate is imaged in the longitudinal plane. In other words, the transducer arrays are aligned, or positioned with respect to one another, so that the transverse imaging array produces an image at (or in the general case, near) the center of the longitudinal image.

Figure 7:
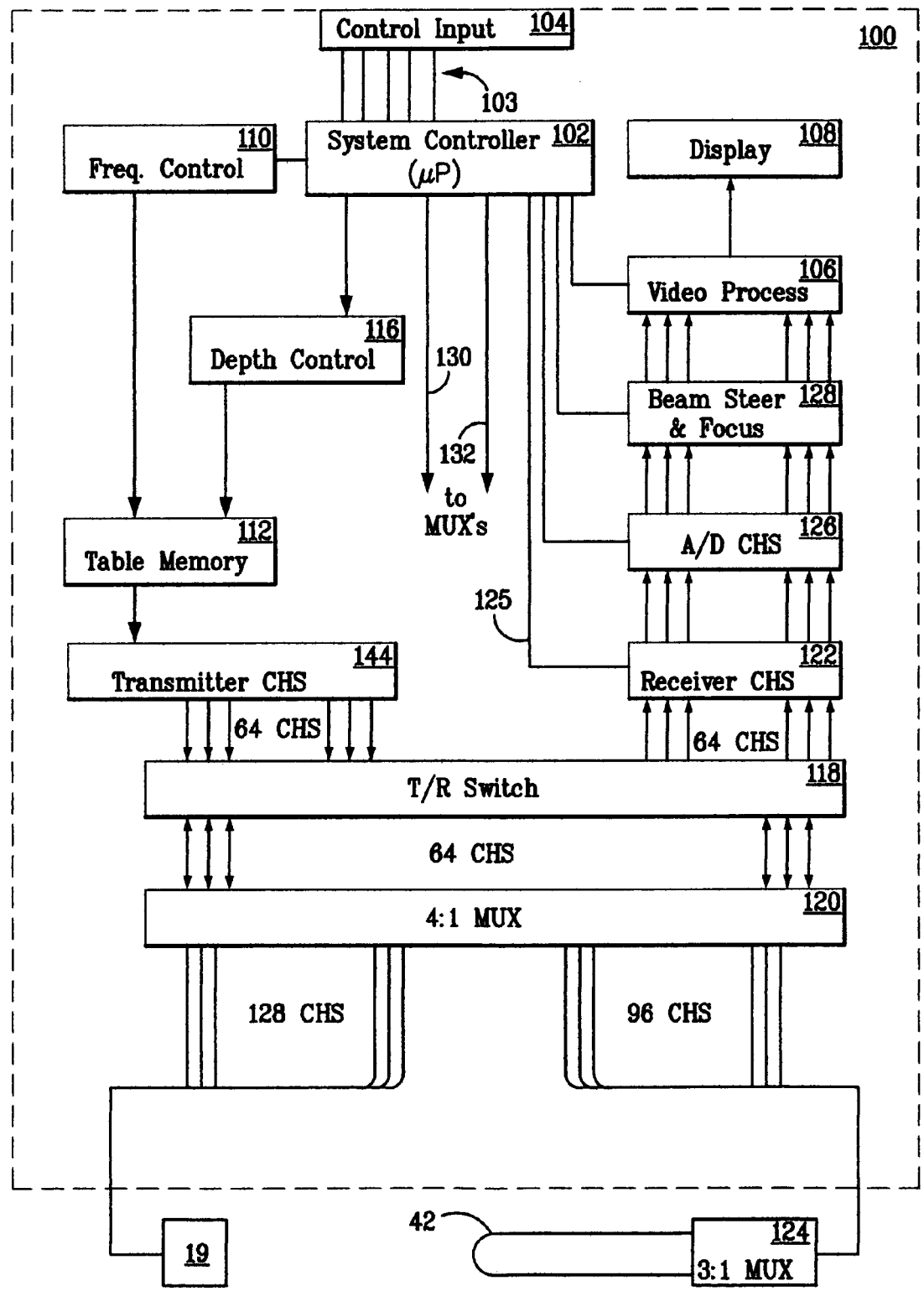
FIG. 7 is block diagram of a system using the ultrasonic probes, in accordance with the invention.

Referring to FIG. 7, ultrasonic transducer 19 and ultrasonic probe 42 are connected to an electronics module 100, which contains the circuitry necessary to excite the ultrasonic transducer 19 and ultrasonic probe 42 so as to send pulses of ultrasound into the patient, receive ultrasound reflected from internal structures and organs, and convert the signals, in a desired fashion to an image or images which may be interpreted in a medically significant fashion. In general, such modules are well known in the art. However, the use of ultrasonic transducer 19 and ultrasonic probe 42 gives rise to a unique arrangement of components.

In general, module 100 may be controlled by a microprocessor 102 connected by suitable lines 103 to a control input 104. Microprocessor 102 and control input 104 may be dedicated, hardwired components (such as a control panel with appropriate switches and knobs for control input 104) within module 100, or may represent, for example a personal computer and a keyboard, respectively, interfaced in a manner well know in the art to the remainder of module 100. If this is the caner suitable software may be provided to allow the keyboard to provide the control inputs typically provided in a modnle 100, such as brightness, contrast, color control, and control over parameter such as frequency of operation, focus, beam steering, system gain, and other necessary parameters, as more fully described below. In a like manner, a video processor 106 and a display 108 may also be dedicated components of the module 100 or the video driver card and monitor of the personal computer.

Frequency control inputs provided by control input 104 are processed by microprocessor 102 and provided in suitable form to a frequency control 110. An output of frequency control 110 determines the rate at which entries in a table memory 112 are read out to each of sixty-four different transmitter channels represented as 114. Table memory 112 includes a multidimensional array of waveform values. The values that are read out for one of the dimensions is determined by a depth control 116, in response to inputs from microprocessor 102, as determined by input from control input 104. Thus the depth of display desired may be adjusted.

The outputs of the transmitter channels are supplied to a transmit/receive switch 118, which is in turn connected to a 4:1 multiplexer or MUX 120 and sixty-four receiver channels, as represented by 122. The transmit/receive switch 118 serves to switch the sixty-four inputs of 4:1 MUX 120 between transmitter channels 114 and receiver channels 122 in a manner well known in the art.

The 4:1 MUX 120 serves to switch the 64 transmitter and receiver channels between 128 elements of transducer 19 (sixty four elements at a time) and the 96 elements of one of the transducer arrays of ultrasonic probe 42. In other words, there are 256 outputs on one side of MUX 120 (the side connected to the cables to transducer 19 and probe 42) and 64 on the other side connected to transmit/receive switch 118. However, in the case of probe 42, some of the outputs are not used. MUX 120 may be a high voltage, low impedance switching multiplexer, such as that manufactured by Supertex, Inc., located in Sunnyvale, Calif., U.S.A.

A second multiplexer or MUX 124 (in this case a 3:1 multiplexer located in the handle of probe 42) having 128 ports on each side, is used to successively connect 96 outputs of MUX 120 to the respective element of the three transducer element arrays of probe 42 described above. MUX 124 may be of the same general type as MUX 120.

Receiver channels 122 provide suitable amplification and conditioning of analog signals returned by transducer elements of transducer 19 and probe 42 in response to reflections of ultrasound by structures within the patient. Gain control signals are provided to receiver channels 122 by a bus 125. The analog signals are converted to digital form by a series of sixty-four analog-to-digital converters or A/D's 126. As is well known in the art, the number of A/D output signals used to form an image is a function of depth of the image, generally with more channels being used for imaging at greater depth. A beam steering and focusing circuit 128 process the digital signals from the A/D's 126. The outputs of beam steering and focusing circuit 128 are provided to video processor 106 to provide a suitable representation of the patient on display 108.

Microprocessor 102 has appropriate outputs 130 and 132 for controlling MWX 120 and MUX 124, as required to perform the sequence of switching described herein.

The images provided on display 108 advantageously include those provided by the three transducer arrays of probe 42, as discussed above. In addition, an image generated by signals from probe 19 may also be displayed, preferably above the image resulting from the signals from probe 42. Thus, in addition to imaging the transverse plane and the entire longitudinal plane of an organ, such as the prostate, or a defined region, a top view may be displayed as well. The various images, when taken together, provide an excellent, very precise view of the organ or image in three dimensions, allowing the precise location of structures and therefore the accurate placement of, for example, seeds or needles, for brachytherapy or cryosurgery, as described above.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An ultrasonic probe comprising:
   an elongate structure having a longitudinal axis;
   a first array of ultrasonic transducer elements extending along an outer surface of said elongate structure in a direction generally parallel to said longitudinal axis;
   a second array of ultrasonic transducer elements extending along the outer surface of the elongate structure in a direction generally parallel to said longitudinal axis; and
   a third array of ultrasonic transducer elements extending about said elongate structure in a direction so that it images a plane perpendicular to that imaged by at least one of said first array and said second array, the third array being disposed in a space between said first array and said second array, wherein said first array, said second array and said third array are outwardly convex arrays, and said first array and said second array are aligned so as to image a portion of a substantially continuous plane perpendicular to said plane imaged by said third array.

2. The probe of claim 1, wherein said third array has a radius of curvature smaller than that of said first array and said second array.

3. The probe of claim 1, wherein said first array and said second array have a radius of curvature of substantially 60 millimeters.

4. The probe of claim 1, wherein said third array has a radius of curvature of substantially 10 millimeters.

5. The probe of claim 1, wherein said first array and said second array are configured so that beams formed by said first array and said second array subtend substantially thirty degrees of arc.

6. The probe of claim 1, wherein said third array is configured so that a beam formed by said third array subtends substantially 180 degrees of arc.

7. The probe of claim 1, further comprising a multiplexer for multiplexing connections to each of said first array, said second array and said third array.

8. The probe of claim 7, wherein said multiplexer is disposed within said elongate structure.

9. The probe of claim 1, wherein each of said first array, said second array and said third array are comprised of transducer elements having a resonant frequency of 6.5 Megahertz.

10. The probe of claim 1, in combination with a second probe, said second probe being capable of positioning so as to imaging in a plane perpendicular to a plane imaged by said first array and a plane imaged by said second array.

11. The combination of claim 10, wherein said second probe comprises transducer elements with a resonant frequency of 6.5 Megahertz.

12. The probe of claim 1, in combination with an electronics module, comprising:
   excitation circuitry for providing excitation energy to said probe;
   receiving circuitry for processing signals received by said probe;
   signal processing circuitry for processing signals from said receiving circuitry to produced processed image signals; and
   a display for displaying the processed image signals.

13. The combination of claim 12, further comprising at least one of:
   frequency setting circuitry for setting a frequency of the excitation energy;
   depth control circuitry for controlling the depth of images produced on said display;
   gain control circuitry for controlling gain of said receiving circuitry; and
   steering and focus control circuitry as a component of said signal processing circuitry for controlling the manner of operation of said signal processing circuitry.

14. The combination of claim 12, wherein said excitation circuitry comprises a table memory for providing values of waveforms used to excite transducer elements of said probe.

15. The combination of claim 12, further comprising analog to digital converters as components of said signal processing circuitry for converting analog signals from said receiving circuitry into digital signals.

16. The probe of claim 1, wherein said first array and said second array hare scanning planes which are co-planar and partially overlap.

17. The probe of claim 16, wherein the scanning planes of the first array and of the second array are configured to allow an entire prostate to be imaged along a single longitudinal plane without moving the probe.

18. An ultrasonic imaging system comprising:
   a first probe having:
      an elongate structure having a longitudinal axis:
      at least a first, array of ultrasonic transducer elements extending along an outer surface of said elongate structure in a direction generally parallel to said longitudinal axis;
      an additional array of ultrasonic transducer elements extending about said elongate structure in a direction so that it images a plane perpendicular to that imaged by said at least one first array;
   a second probe having a further transducer array, said second probe capable of being positioned so as to imaging in a plane perpendicular to a plane imaged by said first array and said plane imaged by said additional array; and an electronics module, said module having:
excitation circuitry for successively exciting said first array, maid additional array and said further array;
receiving circuitry for processing signals received from said first array, said additional array and said further array;
signal processing circuitry for processing signals from said receiving circuitry to produced processed image signals; and
a display for displaying the processed image signals.

19. The system of claim 18, wherein said first probe further comprises:
a second array of ultrasonic transducer elements extending along said outer surface of said elongate structure in a direction generally parallel to said longitudinal axis, said second array also being excited by said excitation circuitry.

20. The system of claim 19, wherein said additional array is disposed between said first array and said second array.

21. The system of claim 18, further comprising at least one multiplexer for connecting each of said first array, said additional array and said further array to said electronics module for display of images.

22. The system of claim 21, wherein said at least one multiplexer comprises:
a first multiplexer for switching said electronics module between said first probe and said second probe; and
a second multiplexer for switching between transducer arrays of said first probe.

23. The system of claim 22, wherein said first multiplexer is a four to one multiplexer, which switches to a first half of transducer element of said further array, a second half of transducer elements of said further array, a first half of transducer element of a selected one of said arrays in said first probe, and a second half of transducer elements of said selected array in said first probe.

24. The system of claim 23, further comprising a second multiplexer for switching said selected array to be one of said first array and said additional array.

25. The system of claim 24, wherein said first probe further comprises:

a second array of ultrasonic transducer elements extending along said outer surface of said elongate structure in a direction generally parallel to said longitudinal axis, said second array also being excited by said excitation circuitry, and said second array is one of said selected arrays.

26. A method for medical ultrasonic imaging comprising:
placing a first probe having transducer arrays which image in two mutually perpendicular directions in a body cavity of a patient;
placing a second probe on an exterior surface of the patient so that a transducer array of said second probe produces an image in a plane perpendicular to each of the two mutually perpendicular planes;
exciting said probes;
forming images using signals from said probes to visualize structures within the patient;
wherein said first probe comprises:
an elongate structure hating a longitudinal axis;
a first array of ultrasonic transducer elements extending along an outer surface of said elongate structure in a direction generally parallel to said longitudinal axis;
a second array of ultrasonic transducer elements extending along said outer surface of said elongate structure in a direction generally parallel to said longitudinal axis; and
a third array of ultrasonic transducer elements extending about said elongate structure in a direction so that it images a plane perpendicular to that imaged bit at least one of said first array and said second array, said third array being disposed in a space between said first array and said second array; and
wherein said exciting said first probe comprises exciting at learnt one of said first array, said second array and said third array.

27. The method of claim 26, wherein said exciting said first probe comprises successively exciting said first array, said second array ant said third array.

* * * * *